United States Patent [19]

Vaisbuch et al.

[11] Patent Number: 5,118,881
[45] Date of Patent: Jun. 2, 1992

[54] PROCESS FOR PREPARING ENVIRONMENTALLY SAFE DICOFOL AND ITS FORMULATIONS

[75] Inventors: Bernard Vaisbuch; Benjamin Shifman, both of Rehovot; Michael Pikarski, Ramat-Gan, all of Israel

[73] Assignee: Agan Chemical Manufacturers, Ltd., Ashdod, Israel

[21] Appl. No.: 611,396

[22] Filed: Nov. 8, 1990

Related U.S. Application Data

[63] Continuation-in-part of Ser. No. 467,461, Jan. 19, 1990, abandoned.

[30] Foreign Application Priority Data

Feb. 13, 1989 [IL] Israel .................................. 89274

[51] Int. Cl.$^5$ .................... C07C 29/74; C07C 29/78
[52] U.S. Cl. .................... 568/810; 568/809; 568/812; 568/841; 568/844
[58] Field of Search ............ 568/809, 810, 812, 841, 568/844, 854, 856, 868, 913, 923

[56] References Cited

U.S. PATENT DOCUMENTS 4,705,902 11/1987 Nichols et al. ................ 568/810

FOREIGN PATENT DOCUMENTS

| 203154 | 9/1955 | Australia | 568/809 |
| 219081 | 4/1957 | Australia | 568/809 |
| 0383054 | 8/1990 | European Pat. Off. | 568/809 |

Primary Examiner—Werren B. Lone
Attorney, Agent, or Firm—Browdy and Neimark

[57] ABSTRACT

The present invention provides for an improved practical process for producing DDTr-free p,p'-dicofol and its formulations substantially free of the practically inactive o-p'-dicofol comprising either directly recrystallizing technical dicofol from a suitable solvent such as acetic acid or alkanes, or alternatively preparing the p,p'-dicofol by the steps of (a) dehydrohalogenating technical DDT to give DDE; (b) chlorinating DDE to give Cl-DDT; and (c) hydrolyzing Cl-DDT to dicofol, wherein the technical DDT is initially recrystallized from a suitable solvent such as lower alkyl alcohols and then recrystallizing the ressulting p,p'-dicofol from a suitable solvent such as acetic acid or alkanes.

14 Claims, No Drawings

PROCESS FOR PREPARING ENVIRONMENTALLY SAFE DICOFOL AND ITS FORMULATIONS

This application is a continuation-in-part of application Ser. No. 07/467,461, filed Jan. 19, 1990, now abandoned.

BACKGROUND OF THE INVENTION

The present invention concerns a process for preparing DDTr-free 1,1-bis-(4-chlorophenyl)-2,2,2-trichloroethanol and formulations substantially free of the practically inactive isomer 1,1-(p-chlorophenyl)-(o-chlorophenyl)-2,2,2-trichloroethanol (o,p-dicofol).

The 1,1-bis-(halophenyl)2,2,2-trichloroethanols are miticidal agents, the preparation of which are described in U.S. Pat. Nos. 2,812,280 and 2,812,362. 1,1-bis-(chlorophenyl)-2,2,2-trichloroethanol (dicofol) is an effective acaricide and it and compositions containing dicofol are extensively used in agriculture and horticulture. The present commercial process for manufacturing 1,1-bis-(chlorophenyl)-2,2,2-trichloroethanol (dicofol) uses 1,1-bis-(chlorophenyl)-2,2,2-trichloroethane (DDT) as the starting material. DDT is dehydrohalogenated with alkali to afford 1,1-bis-(chlorophenyl)-dichloroethylene (DDE), which is chlorinated to afford 1,1-bis-(chlorophenyl)-1,2,2,2-tetrachloroethane (Cl-DDT). The 1,1-bis-(chlorophenyl)-1,2,2,2-tetrachloroethane is then converted via hydrolysis to the desired product, dicofol.

Technical dicofol made by this process contains from about 2% to about 10% (typically 7%) of DDT-related impurities (DDTr's).

The DDTr's which are encountered in the present commercial process to manufacture dicofol include: 1,1-bis-(4-chlorophenyl)-2,2,2-trichloroethane (p,p'-DDT); 1,-(4-chlorophenyl)-1-(2-chlorophenyl)-2,2,2-trichloroethane o,p-DDT); 1,1-bis-(4-chlorophenyl)-2,2-dichloroethylene (p,p'-DDE); 1-(4-chlorophenyl-1-(2-chlorophenyl)-2,2-dichloroethylene (o,p'-DDE); 1,1-bis-(4-chlorophenyl)-2,2-dichloro ethane (p,p'-DDD); 1-(4-chlorophenyl)-1-(2-chlorophenyl)-2,2-dichloroethane (o,p'-DDD); 1,1-bis (4-chlorophenyl)-1,2,2,2-tetrachloroethane (p,p'-Cl-DDT); 1-(4-chlorophenyl)-1-(2-chlorophenyl-1,2,2,2-tetrachloroethane (o,p'-Cl-DDT). Non-DDTr impurities which are encountered in the present commercial process used to manufacture dicofol include: 4,4'-dichlorobenzophenone (p,p'-DCBP); 2,4'-dichlorobenzophenone (o,p'-DCBP); 4,4'-dichlorobenzyl (p,p'-DCBZ); and 2,4'-dichlorobenzyl (o,p'-DCBZ). DDTr's are present along with the desired dicofol product due to the impurity of DDT used as a starting reactant and formation during the conversion of DDT to dicofol. As a group, DDTr's are suspected of posing an environmental risk.

Accordingly, it is desirable to find means to eliminate or reduce these DDTr impurities.

Recently, U.S. Pat. No. 4,705,902 described a process for preparing DDTr-free dicofol using selective solvent extraction. However, even the product of this extraction process is a mixture of isomers and still contains some 15% of the o,p'-dicofol. In addition, this product is a semi-liquid/waxy, odiferous, brown substance, which must be heated to a melt for dispensing and formulation and can only be shipped in drums, said drums then being a considerable environmental problem. The waxy state of the product also makes it very difficult to formulate as a flowable powder.

OBJECTIVES OF THE INVENTION

It is the objective of the present invention to provide a process for preparing 1,1-bis-(p-chlorophenyl)-2,2,2-trichloroethanol (p,p'-dicofol) substantially free of DDTr's and the practically inactive o',p-dicofol. It is an objective of the present invention to also provide a formulation of p,p'-dicofol substantially free of DDTr's and the practically inactive o,p-dicofol, which can be readily formulated as a flowable powder. A further objective is the provision of a formulation of p,p'-dicofol which can be used at lower application rates than the dicofol currently available, thereby reducing the chances of any environmental contamination. These and other objectives of the invention will become apparent to those skilled in the art from the following description.

SUMMARY OF THE INVENTION

In accordance with the present invention there is provided an improved practical process for producing DDTr-free p,p'-dicofol substantially free of the practically inactive o,p'-dicofol comprising either directly recrystallizing technical dicofol from a suitable solvent such as acetic acid or alkanes, or alternatively preparing the p,p'-dicofol by the steps of a. dehydrohalogenating technical DDT to give DDE;
b. chlorinating DDE to give Cl-DDT; and
c. hydrolyzing Cl-DDT to dicofol;

wherein the improvement consists of initially recrystallizing the technical DDT from a suitable solvent such as lower alkyl alcohols and then recrystallizing the resulting p,p'-dicofol from a suitable solvent such as acetic acid or alkanes.

The pure p,p'-dicofol produced by this invention is a crystalline powder which is more easily and more safely formulated without having to be subjected to heating and melting, as required by the current commercially available technical dicofol.

The present invention also provides an improved DDTr-free acaricidal composition containing a solid or liquid carrier and an acaricidally effective amount of p,p'-dicofol substantially free of the practically inactive o,p-dicofol.

DETAILED DESCRIPTION OF THE INVENTION

Technical dicofol actually is a mixture of p,p'-dicofol and o,p'-dicofol containing 2% to 20% -typically 10%-15% - of o,p'-dicofol, as well as DDT-related compounds. The latter compounds can be removed as already described in U.S. Pat. No. 4,705,902. However, even after subjecting technical dicofol to the process of this U.S. patent, the dicofol still remains a mixture containing some 15% o,p'-dicofol.

The present invention has surprisingly discovered that the o,p'-dicofol is practically inactive. Thus, even after subjecting technical dicofol to the process of U.S. Pat. No. 4,705,902, the resulting dicofol still contains some 15% of practically inactive material.

The present invention is able to overcome this problem and has developed a process to remove simultaneously both the DDT's and the practically inactive o,p'-dicofol from dicofol, affording essentially pure, environmentally acceptable p-p'-dicofol. The present invention can be effected by either directly recrystallizing technical dicofol commercially available, or by first purifying DDT via crystallization, processing the resulting p,p'-DDT to p,p-dicofol and recrystallizing the resulting p,p'-dicofol.

One approach consists of directly recrystallizing technical dicofol containing both o,p'-dicofol and p,p'-dicofol from a suitable solvent chosen from the group consisting of alkanes having from 1 to 10 carbon atoms, xylene and acetic acid. Typical alkanes useful for the present invention are normal or cyclo-alkanes such as pentane, hexane, heptane, octane, iso-octane, decane, or mixtures thereof. Preferred solvents are acetic acid, heptane or hexane, with acetic acid being the most preferred.

With one recrystallization removes almost all of the o,p-dicofol and DDTr's, it is usually necessary to recrystallize the technical dicofol twice to give essentially 99% pure p,p'-dicofol and to drop the concentration of DDTr's to less than 0.1%.

Benzyl very often is an impurity in technical dicofol. Therefore, prior to the above described purification process, it may be necessary to remove the benzyl by first recrystallizing the technical dicofol from a solvent such as isobutanol or isopropanol, with the latter being the preferred solvent.

The first process of the present invention has the distinct advantage of involving essentially one stage. However, the losses during recrystallization sometimes approach 50%. This can be a commercial disadvantage, as one starts from the relatively expensive technical dicofol.

A second, alternative approach of the present invention consists of starting from technical DDT, dehydrohalogenating the technical DDT to give DDE, chlorinating DDE to give Cl-DDT and hydrolyzing Cl-DDT to give dicofol where the improvement consists of first recrystallizing the DDT from a solvent chosen from the group consisting of lower alkyl alcohols, and recrystallizing the resulting p,p'-dicofol from a suitable solvent useful in the above-mentioned direct process. Typical lower alkyl alcohols useful in the present invention are methanol, ethanol, propanol, n-butanol, or isobutanol, n-butanol and isobutanol are preferred, with isobutanol being most preferred.

The advantage of this second approach of the present invention is, that one starts from the relatively inexpensive technical DDT, where the overall loss in production is in the order of about 20%. In addition, the reactions starting with the single p,p'-DDT isomer is advantageous in that one can optimize the reaction conditions at each stage, thereby avoiding and/or diminishing the formation of DDTr's.

The second approach can also be effected by purifying any of the intermediate compounds such as DDE or Cl-DDT by recrystallization from a suitable solvent. However, such an approach is less effective, since one will have to get rid of DDTr's already formed with the attendant higher losses, if additional recrystallizations are required.

It is to be noted that both processes of the present invention simultaneously remove the practically inactive o,p'-dicofol, affording essentially pure (99%) p,p'-dicofol while lowering the DDTr concentration to the environmentally acceptable less than 0.1%, as required by the PA in the USA. The product from either process is a white, odorless powder, with a definite melting point above 70° C., easy to handle and can be packed in bags. On the other hand, commercial dicofol is a semi-liquid of the consistency of honey, which must be heated in order to be handled. Such further heating may very possibly form additional DDTr's.

The present invention further provides an improved DDTr-free acaricidal composition whose active ingredient is essentially pure p,p'-dicofol. This has the dual advantage of being able to use lower application rates of dicofol than currently in use, while being able to avoid contaminating the environment with the practically inactive o-p'-dicofol.

The p,p'-dicofol of the present invention may be formulated with diluents, carriers, solvents, wetting agents, dispersing agents, fungicides, or insecticides in dusts, wettable powders, or salt emulsifying concentrates, as described in U.S. Pat. No. 2,812,280, whose contents are incorporated by mention into the present invention. Isolation and use of the essentially pure p,p'-dicofol enables one in particular to easily prepare solid, dry wettable powder formulations. Such formulations may contain a very high concentration of p,p'-dicofol, typically 70% to 90% active ingredient.

While the invention will now be described in connection with certain preferred embodiments in the following examples it will be understood that it is not intended to limit the invention to these particular embodiments. On the contrary, it is intended to cover all alternatives, modifications and equivalents as may be included within the scope of the invention as defined by the appended claims. Thus, the following examples which include preferred embodiments, will serve to illustrate the practice of this invention, it being understood that the particulars shown are by way of example and for purposes of illustrative discussion of preferred embodiments of the present invention only and are presented in the cause of providing what is believed to be the most useful and readily understood description of procedures as well as of the principles and conceptual aspects of the invention.

EXAMPLE 1

Biological Testing of p,p'-Dicofol vs. o,p'-Dicofol

An EC formulation containing 180 g active material per liter, 2.8 g Berol 255 (Berol Co. brand of non-ionic alkyl phenol polyglycolic ether with hydrophobic part dionyl phenol ethoxylate with average chain longer than 100 moles of ethylene oxide), 4.2 Berol 822 (Berol Co. brand of emulsifier of alkyl aryl sulfonate types) and xylene to 100 cc was diluted with water to obtain a solution containing 360 ppm. Leaves from bean plants grown under controlled conditions were sprayed on both sides with this diluted solution. Discs of 3 cm in diameter were cut from the leaves after they were dried at room temperature. These discs were placed in special isolated cages. On each disc were placed ten mature mites and the cages with the mites were kept at 25° C. amd a relative humidity of 45%–55%. After 48 hours the death rate of the mites was counted. The results are listed in Table 1. The conclusively shows the very high kill rate of pure p,p'-dicofol and the complete inactivity of the pure o,p'-dicofol at such a low application rate, with the latter having even a lower repulse rate than the "blank".

EXAMPLE 2

Direct Recrystallization of Technical Dicofol

Into a 500 ml flask was added 400 g technical dicofol (after removal of benzyl), containing about 15% o,p'-dicofol and about 6% DDTr impurities. To this was added 250 ml glacial acetic acid and the mixture heated to 40° C.–45° C. until a clear solution resulted. The mixture was cooled to 20° C., stirred for 4 hours and further cooled at 17° C. The resulting crystals were filtered and the cake washed with additional acetic acid, cooled at 17° C. to afford 200 g p,p'-dicofol containing some 0.58% DDTr impurities. This product was again recrystallized as above, to afford about 150 g p,p'-dicofol, having a purity of 99% (via liquid chromatography), containing 0.06% DDTr impurities.

About 110 ml xylene was added and the mixture washed with NaHCO$_3$ solution and finally with water until a pH of 7 is reached. The xylene is removed under vacuum to yield 335 g technical p,p'-dicofol.

e. Removal of Benzyl

The technical p,p'-dicofol from Stage (d) was treated with 280 ml isopropanol, the mixture cooled to 10° C. and the benzyl precipitated out. The benzyl was filtered and the isopropanol removed under vacuum to afford 320 g p,p'-dicofol having a purity of 97% containing 0.5% DDTr impurities.

f. Final Purification of p,p'-Dicofol

Following the method of Example 2, 578 g of the p,p'-dicofol from Stage (e) was recrystallized from glacial acetic acid to yield 436 g p,p'-dicofol having a purity of 99% (via liquid chromatography), containing

TABLE 1

RESULTS OF BIOLOGICAL TESTING OF SEPARATE FORMULATIONS OF p,p'-DICOFOL AND o,p'-DICOFOL

| Experiment | Control[a] | | | Blank[b] | | | 99.5% p,p'-dicofol | | | 99.5% o,p'-dicofol | | |
|---|---|---|---|---|---|---|---|---|---|---|---|---|
| No. | Live | Dead | Repulsed[c] | Live | Dead | Repulsed | Live | Dead | Repulsed | Live | Dead | Repulsed |
| 1 | 9 | 0 | 1 | 10 | 0 | 0 | 1 | 9 | 0 | 8 | 0 | 2 |
| 2 | 9 | 0 | 1 | 10 | 0 | 0 | 0 | 10 | 0 | 8 | 0 | 2 |
| 3 | 10 | 0 | 0 | 7 | 1 | 2 | 0 | 10 | 0 | 10 | 0 | 0 |
| 4 | 10 | 1 | 0 | 7 | 2 | 1 | 0 | 10 | 0 | 9 | 0 | 1 |
| 5 | 8 | 0 | 1 | 9 | 1 | 0 | 0 | 10 | 0 | 9 | 0 | 1 |
| 6 | 8 | 0 | 2 | 4 | 0 | 6 | 2 | 8 | 0 | 9 | 0 | 1 |
| 7 | 8 | 0 | 2 | 7 | 0 | 3 | 0 | 9 | 1 | 6 | 0 | 4 |
| 8 | 9 | 0 | 1 | 8 | 0 | 2 | 0 | 10 | 0 | 9 | 0 | 1 |
| 9 | 8 | 1 | 1 | 5 | 2 | 3 | 0 | 10 | 0 | 8 | 0 | 2 |
| 10 | 9 | 0 | 1 | 7 | 1 | 2 | 0 | 10 | 0 | 9 | 0 | 1 |
| TOTAL | 88 | 2 | 10 | 74 | 7 | 19 | 3 | 96 | 1 | 85 | 0 | 15 |
| Percent | 88% | 2% | 10% | 74% | 7% | 19% | 3% | 96% | 1% | 85% | 0 | 15% |

[a]Control: not sprayed at all.
[b]Blank: sprayed with solvent and other ingredients, but without the active compound.
[c]Dropped off into the water.

EXAMPLE 3

Pure p,p'-Dicofol Starting From Technical DDT a. Recrystallization of Technical DDT Into a 2 liter flask is added 1,500 ml isobutanol, which is heated to 60° C. To this is added 600 g technical DDT (containing about 80% p,p'-DDT), the mixture heated until a clear solution is obtained, then cooled with vigorous stirring to 20° C. and then filtered. This yields 430 g DDT containing 97.6% p,p'-DDT and 1.2% o,p-DDT. This was again recrystallized from 800 ml isobutanol to afford 375 g DDT containing 99.5% p,p'-DDT.

b. Dehydrohalogenation of p,p'-DDT

The p,p'-DDT from Stage (a) is placed into a 500 ml flask, some 3 ml polyethylene glycol is added, the mixture is heated to 100° C. and about 80 ml of a 46% NaOH solution is added dropwise. The temperature increases to about 120° C. and after 3–4 hours, when the reaction is completed, the resulting product is washed with water until a pH of 7. This yields 325 g p,p'-DDE with a purity of 99.7%.

c. Chlorination of p,p'-DDE

Onto the p,p'-DDE obtained in Stage (b) 100 ml water is added, the mixture heated to 80° C.–85° C. and chlorine gas added over a period of 8–11 hours, until the concentration of p,p'-DDE drops to 0.2%. The upper aqueous phase is separated to afford 410 g p,p'-DDT, which was used directly in the next stage.

d. Hydrolysis of p,p'-Cl-DDT to p,p'-Dicofol

Onto the p,p'-ClDDT of Stage (c) was added 17% p-toluenesulphonic acid, the mixture heated to 145° C.–148° C. and the reaction run for 8–9 hours until the concentration of p,p'-ClDDT drops to about 0.2%.

0.044% DDTr impurities.

EXAMPLE 4

Formulations of p,p'-Dicofol

Several wettable powder formulations of essentially pure p,p'-dicofol were prepared as listed in Table 2. The results were equal to or better than formulations containing up to 15% of the practically inactive o,p-dicofol when used against mites.

TABLE 2

WETTABLE POWDER FORMULATIONS OF p,p'-DICOFOL

| Ingredient | 50 W.P. Composition (%) | 60 W.P. Composition (%) | 80 W.P. Composition (%) |
|---|---|---|---|
| p,p'-dicofol (97%–99%) | 50.5 | 61.9 | 82.5 |
| REAX 45T[a] | 5 | 6 | 6 |
| VANISPERSE[b] | 1.5 | 1.5 | 1.5 |
| WESSALON S[c] | 10 | 10 | 10 |
| Kaoline | 33 | 20.6 | — |

[a]West Vaco Co. brand of a mixture of sugar free sodium lignosulfonate and sodium alkyl naphthalene sulfonate.
[b]Borregard Co. brand of sodium magnesium sulfonate increase number of functional phenolic hydroxyl n-carboxylic groups.
[c]Degussa brand of silicic acid.

EXAMPLE 5

Comparison of Activities of o,p'-Dicofol and p,p'-Dicofol with Commercial Dicofol at Various Dosages The activity of essentially pure o,p'-dicofol and p,p'-dicofol were compared with the activity of commercial dicofol containing about 15% o,p'-dicofol at application rates of 2,000 ppm, 1,000 ppm, 500 ppm and 100 ppm active material as follows:

Some 50 mg of each compound was completely dissolved in 1 ml of a mixture of acetone/emulgater (1:1). To this solution was added 25 ml distilled water containing 50 microliters of an organosilicon surfactant. This yields a solution containing 0.2% of active material. Lower doses were obtained via dilution with distilled water. The control contained only water, emulgator and surfactant.

Red mites that were grown on bean plants from Neve Ya'ar Forest were used for this study. Leaves from bean plants were sprayed with the solution to be tested, using a volume of 2.5 ml on each side of the leaf. The leaves were placed on water soaked paper in petri dishes. Some two hours after spraying (after the sprayed solution had dried) 20 mites were placed on each leaf and kept at a temperature of 27° C. The death rate of the mites in percent were checked 24 hours after spraying. The results appear in Table 3. These results conclusively show the great advantage of using a fomulation containing essentially pure p,p'-dicofol—especially at very low application rates—and the ineffectiveness of commercial dicofol at such low application rates.

TABLE 3

KILL RATE (IN %) OF o,p'-DICOFOL, p,p'-DICOFOL AND COMMERCIAL DICOFOL AT DIFFERENT APPLICATION RATES.

| Compound | Application Rate in ppm | | | | | | | |
|---|---|---|---|---|---|---|---|---|
| | 2,000 | | 1,000 | | 500 | | 100 | |
| Dicofol | 100 | 100 | 100 | 100 | 70 | 85 | 20 | 20 |
| p,p'-Dicofol | 100 | 100 | 100 | 100 | 100 | 100 | 50 | 70 |
| o,p'-Dicofol | 80 | 80 | 40 | 80 | 30 | 20 | 20 | 0 |
| Control | 0 | 0 | 0 | 0 | 5 | 0 | 0 | 0 |

We claim:

1. A process for preparing DDTr-free p,p'-dicofol substantially free of the practically inactive o,p'-dicofol comprising recrystallizing technical dicofol from acetic acid.

2. A process in accordance with claim 1, wherein said recrystallizing is carried out twice.

3. A process in accordance with claim 1, wherein the technical dicofol contains from 2% to 20% o,p'-dicofol.

4. A process in accordance with claim 1, wherein benzyl is removed from said technical dicofol prior to said crystallization.

5. A process for preparing DDTr-free p.p'-dicofol substantially free of the practically inactive o.p'-dicofol, comprising recrystallizing technical dicofol from glacial acetic acid, to afford 98+% p,p'-dicofol, containing less than 0.1% DDTR's.

6. A process in accordance with claim 5, wherein the technical dicofol contains from 2% to 20% o,p'-dicofol.

7. In a process for preparing DDTr-free p,p'-dicofol substantially free of the practically inactive o,p'-dicofol from DDT, the improvement consisting of:
initially recrystallizing technical DDT from a lower alkyl alcohol to obtain essentially pure p,p'-DDT, and recrystallizing the resultant mixture of o,p'-dicofol and p,p'-dicofol from acetic acid.

8. A process in accordance with claim 7, wherein the lower alkyl alcohol is selected from the group consisting of methanol, ethanol, propanol, butanol, isobutanol, and mixtures thereof.

9. A process in accordance with claim 7, wherein the lower alkyl alcohol is isobutanol.

10. A process in accordance with claim 7, wherein said recrystallizing of said technical DDT is carried out twice.

11. A process for obtaining substantially pure p,p'-dicofol from a starting material of technical dicofol, comprising:
mixing said technical dicofol with a solvent consisting essentially of acetic acid and heating the mixture until a clear solution is obtained;
cooling said clear solution to effect precipitation of crystals from said solution; and
recovering said crystals.

12. A process according to claim 11 wherein said acetic acid is glacial acetic acid.

13. A process according to claim 11 further comprising washing said crystals with cold acetic acid; and recrystallizing said washed crystals by again mixing said washed crystals with acetic acid, heating to form a clear solution, cooling to precipitate crystals, and recovering said crystals having a purity of approximately 99% p,p'-dicofol.

14. In a process for preparing DDTr-free p,p'-dicofol substantially free of the practically inactive o,p'-dicofol from DDT, the improvement consisting of:
initially recrystallizing technical DDT twice from isopropanol to obtain essentially pure p,p'-dicofol and p,p'-dicofol from glacial acetic acid to provide p,p'-dicofol having a purity of 99% containing less than 0.1% DDTr's.

* * * * *

UNITED STATES PATENT AND TRADEMARK OFFICE
CERTIFICATE OF CORRECTION

PATENT NO. : 5,118,881

DATED : June 2, 1992

INVENTOR(S) : VAISBUCH ET AL

It is certified that error appears in the above-identified patent and that said Letters Patent is hereby corrected as shown below:

| | |
|---|---|
| Column 3, line 16 | Delete "with", insert therefor -- While -- |
| Column 3, line 44 | Delete "or isobutanol, n-butanol", insert therefor -- or isobutanol. n-Butanol -- |
| Column 3, line 66 | Delete "PA", insert therefor -- EPA -- |
| Column 4, line 50 | Delete "dionyl", insert therefor -- dinonyl -- |
| Column 4, line 64 | Delete "The conclusively", insert therefor -- This conclusively -- |

UNITED STATES PATENT AND TRADEMARK OFFICE
CERTIFICATE OF CORRECTION

PATENT NO. : 5,118,881

DATED : June 2, 1992

INVENTOR(S) : VAISBUCH, ET AL

It is certified that error appears in the above-identified patent and that said Letters Patent is hereby corrected as shown below:

Column 7, line 13      Delete "acetone/emulgater", insert therefor -- acetone/emulsifier --

Column 8, lines 49 & 50      Delete "isopropanol to obtain essentially pure p,p'dicofol and p,p'-dicofol from glacial acid to provide", insert therefor -- isopropanol to obtain essentially pure p,p'-DDT and recrystallizing the resultant mixture of o,p'-dicofol and p,p'-dicofol from glacial acetic acid to provide --

Signed and Sealed this

Fifth Day of October, 1993

Attest:

BRUCE LEHMAN

Attesting Officer      Commissioner of Patents and Trademarks